United States Patent
Bikkina et al.

(10) Patent No.: US 9,645,067 B2
(45) Date of Patent: May 9, 2017

(54) METHOD AND DEVICE FOR DETERMINING SOLID PARTICLE SURFACE ENERGY

(71) Applicant: University of Tulsa, Tulsa, OK (US)

(72) Inventors: Prem Kumar Bikkina, Tulsa, OK (US); Ram S. Mohan, Broken Arrow, OK (US); Ovadia Shoham, Tulsa, OK (US); Luis Eduardo Gomez, Tulsa, OK (US); Hariprasad Janakiram Subramani, Houston, TX (US); Gene Edward Kouba, Houston, TX (US)

(73) Assignee: UNIVERSITY OF TULSA, Tulsa, OK (US)

( * ) Notice: Subject to any disclaimer, the term of this patent is extended or adjusted under 35 U.S.C. 154(b) by 0 days.

(21) Appl. No.: 15/217,897

(22) Filed: Jul. 22, 2016

(65) Prior Publication Data

US 2016/0334318 A1  Nov. 17, 2016

Related U.S. Application Data (62) Division of application No. 14/450,055, filed on Aug. 1, 2014, now Pat. No. 9,417,175.

(Continued)

(51) Int. Cl.
| | | |
|---|---|---|
| *G01N 13/00* | (2006.01) | |
| *G01N 13/02* | (2006.01) | |
| *B03D 1/02* | (2006.01) | |

(52) U.S. Cl.
CPC ............ *G01N 13/02* (2013.01); *B03D 1/02* (2013.01); *B03D 1/028* (2013.01); *G01N 13/00* (2013.01); *G01N 2013/0233* (2013.01)

(58) Field of Classification Search
CPC .......... G01N 13/00; G01N 33/24; G01N 5/00; G01N 2001/2866; E21B 43/16; E21B 43/20; B03D 1/00; B44D 3/127
See application file for complete search history.

(56) References Cited

U.S. PATENT DOCUMENTS

| | | | |
|---|---|---|---|
| 2003/0015542 A1* | 1/2003 | Nulty | B44D 3/127 220/780 |
| 2004/0055259 A1* | 3/2004 | Caruso | B44D 3/127 53/471 |

(Continued)

OTHER PUBLICATIONS

Article titled "Fundamentals of Adhesion" by 3M published at least by Sep. 26, 2016.*

(Continued)

*Primary Examiner* — Blake A Tankersley
(74) *Attorney, Agent, or Firm* — King & Spalding LLP (57) ABSTRACT

A wedge floatation device includes a bottom section and a sidewall positioned around a perimeter of the bottom section to contain a liquid within the wedge floatation device. The bottom section includes an outer portion and a plateau portion centrally positioned in the bottom section. The plateau portion is raised to a height above the outer portion and below a top edge of the sidewall. The plateau portion includes a groove that is substantially concentric with an outer perimeter of the plateau portion. The groove is designed to dampen the velocity of a liquid directed from the outer perimeter of the plateau portion to a center of the plateau portion. The bottom section further includes a transition portion extending between the outer portion and the plateau portion. The transition portion surrounds the outer perimeter of the plateau portion. The outer portion surrounds a perimeter of the transition portion.

10 Claims, 6 Drawing Sheets

Related U.S. Application Data (60) Provisional application No. 61/861,284, filed on Aug. 1, 2013.

(56) References Cited

U.S. PATENT DOCUMENTS

| | | |
|---|---|---|
| 2004/0255650 A1 | 12/2004 | Moudgil |
| 2011/0106456 A1 | 5/2011 | Szabo |
| 2012/0152547 A1 | 6/2012 | Hinkel |
| 2015/0075962 A1 | 3/2015 | Shimoyama |

OTHER PUBLICATIONS

International Search Report for PCT/US2014/049467, mailed Nov. 4, 2014.
Dang-Vu T et al: "Wettability determination of solids isolated from oil sands." Colloids and Surfaces. A, Physicachemical and Engineering Aspects, Elsevier, Amsterdam, NL. vol. 337, No. 1-3, Apr. 1, 2009. (Apr. 1, 2009), pp. 80-90, XP025914649, ISBN: 0927-7757, DOI: 10.2016/J. Colsurfa. 2008.11.055 [retrieved on Dec. 6, 2008] paragraph [03.6]; figure 2.
D.W. Fuerstenau et al.: "Characterization of the wettability of solid particles by film flotation 1. Experimental investigation", Colloids and Surfaces, vol. 60, Nov. 1, 1991 (Nov. 1, 1991), pp. 127-144, XP055146003, ISSN: 0166-6622, DOI: 10.1016/0166-6622 (91)80273-Q, p. 128, paragraph 2, p. 130, paragraph 3.
Renhe Jia et al.: "Chemical Reagents for Enhanced Coal Flotation", International Journal of Coal Preparation and Utilization, vol. 22, No. 3, May 1, 2002 (May 1, 2002), pp. 123-149, XP009114000, ISSN: 0734-9343, DOI: 10.1080/07349340213847 p. 128, paragraph 2.
Wu Y et al: "An experimental study of wetting behavior and surfactant EOR in carbonates with model compounds", S P E Journal, Society of Petroleum Engineers, Inc. US, vol. 13, No. 1, Mar. 1, 2008 (Mar. 1, 2008), pp. 26-34, XP008172847, ISSN: 1086-055X, DOI: 10.2118/99612-PA the whole document.

* cited by examiner

METHOD AND DEVICE FOR DETERMINING SOLID PARTICLE SURFACE ENERGY

CROSS-REFERENCE TO RELATED APPLICATIONS

The present application is a divisional of and claims priority to U.S. patent application Ser. No. 14/450,055, filed Aug. 1, 2014, and titled "Method and Device for Determining Solid Particle Surface Energy," which claims priority under 35 U.S.C. Section 119(e) to U.S. Provisional Patent Application No. 61/861,284, filed Aug. 1, 2013, and titled "Design and Experimental Procedure of Solid Particle Surface Energy Measurement," the entire contents of which are incorporated herein by reference.

TECHNICAL FIELD

The present disclosure relates generally to determining the surface energy of solid particles and more particularly to a method and device for determining surface energy of solid particles.

BACKGROUND

The wettability of solid particles, which is related to the surface energy of the solid particles, is an important parameter in many industrial applications. For example, separation of different solid particles from a mixture may be performed based on their wettability. Thus, a reliable and efficient method and device for quantifying wettability may have useful industrial applications.

Existing methods of determining surface energy of solid particles and thus quantifying wettability have several limitations. For example, one conventional method of solid particle surface energy measurement is known as the Film Floatation Technique. The Film Floatation Technique involves careful placement/sprinkling of a known weight of particles on the surface of a known surface tension liquid. However, the Film Floatation Technique has a number of limitations. For example, the Film Floatation Technique requires large volumes of liquids to implement the method, which results in a need for subsequent disposal of large volumes of the liquids. The results of the Film Floatation Technique may also have a large degree of uncertainty. Another limitation of the Film Floatation Technique is related to the experimental difficulties associated with sprinkling/placing solid particles on a liquid surface such that the kinetic energy component of the particle striking/touching the liquid surface would not dominate the surface tension component of the liquid. The concern associated with the dominance of the kinetic energy component of the particle over the surface tension component may be particularly pronounced if the particles are sizes ranging from few tens of microns to few hundred microns. For example, some solid particles may sink in the liquid as a result of the kinetic energy associated with the placement of the solid particles on the liquid surface instead of the surface energy of the solid particles. Another limitation of the Film Floatation Technique is the requirement to collect subsequent separation of sinking and floating solid particles and measure their weights.

Accordingly, solid particle surface energy measurement methods and devices that reduce measurement uncertainties and difficulties associated with existing methods and devices are desirable.

SUMMARY

The present disclosure relates generally to determining the surface energy of solid particles. In an example embodiment, a method of determining solid particle surface energy includes placing solid particles in a container made of a very high surface energy material and pouring a liquid into the container. The method further includes tilting the container to drain out from the container a first subset of the solid particles floating at a top surface of the liquid and tilting the container to move the liquid away from a second subset of the solid particles that are below the top surface. The method also includes tilting the container to move the liquid back toward the second subset of the solid particles such that at least a portion of the second subset of particles floats at the top surface of the liquid and tilting the container to drain out from the container the portion of the second subset of the solid particles now floating at the top surface of the liquid.

In another example embodiment, a wedge floatation device includes a bottom section and a sidewall positioned around a perimeter of the bottom section to contain a liquid within the wedge floatation device. The bottom section includes an outer portion and a plateau portion centrally positioned in the bottom section. The plateau portion is raised to a height above the outer portion and below a top edge of the sidewall. The plateau portion includes a groove that is substantially concentric with an outer perimeter of the plateau portion. The groove is designed to dampen the velocity of a liquid directed from the outer perimeter of the plateau portion to a center of the plateau portion. The bottom section further includes a transition portion extending between the outer portion and the plateau portion. The transition portion surrounds the outer perimeter of the plateau portion, and the outer portion surrounds a perimeter of the transition portion.

These and other aspects, objects, features, and embodiments will be apparent from the following description and the appended claims.

BRIEF DESCRIPTION OF THE DRAWINGS

Reference will now be made to the accompanying drawings, which are not necessarily drawn to scale, and wherein.

The drawings illustrate only example embodiments and are therefore not to be considered limiting in scope. The elements and features shown in the drawings are not necessarily to scale, emphasis instead being placed upon clearly illustrating the principles of the example embodiments.

DETAILED DESCRIPTION OF THE EXAMPLE EMBODIMENTS

In the following paragraphs, particular embodiments will be described in further detail by way of example with reference to the drawings. In the description, well-known components, methods, and/or processing techniques are omitted or briefly described. Furthermore, reference to various feature(s) of the embodiments is not to suggest that all embodiments must include the referenced feature(s).

Figure 1:
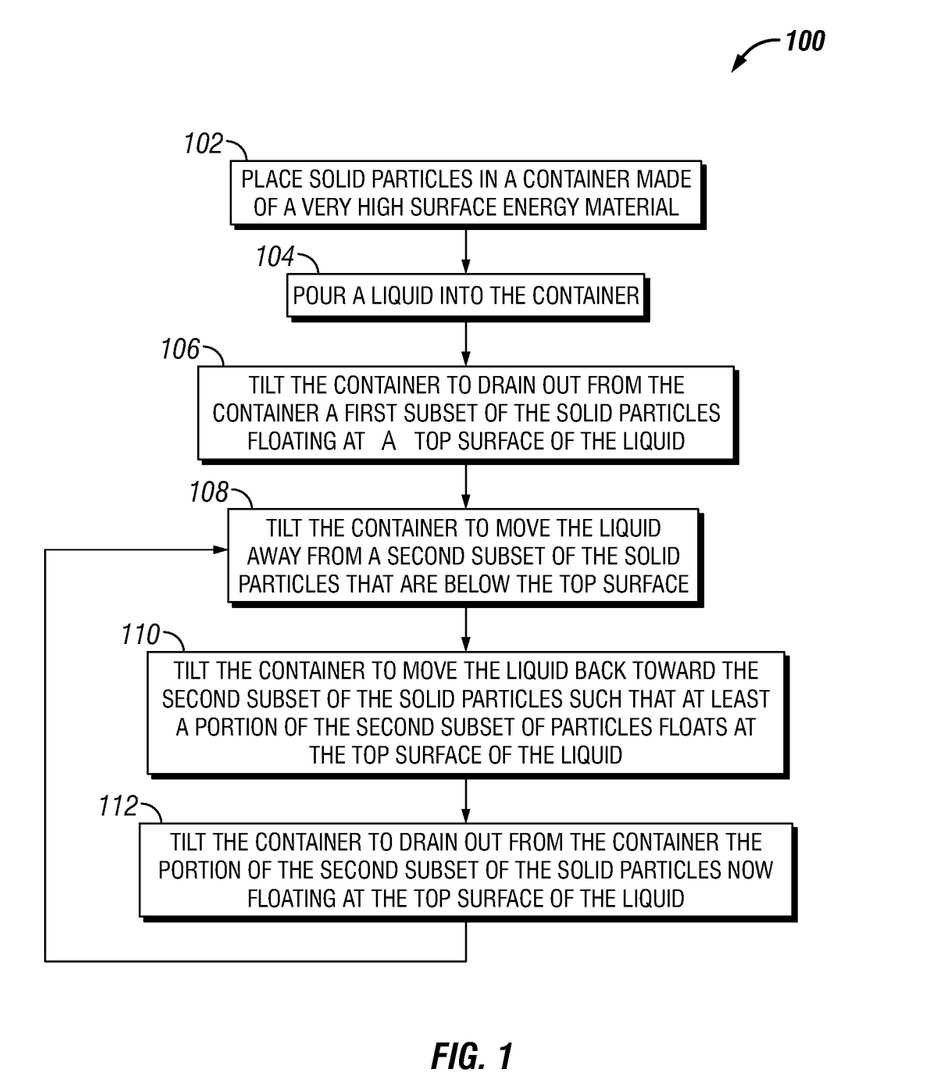
FIG. 1 illustrates a method for determining solid particle surface energy according to an example embodiment.

Turning now to the drawings, FIG. 1 illustrates a method 100 for determining solid particle surface energy according to an example embodiment. The method 100 is described below using glass beads as a non-limiting illustrative example of solid particles. In particular, the method 100 is described below with respect to surface treated and untreated glass beads as well as various concentrations of aqueous methanol solutions. For example, the various concentrations of aqueous methanol solutions may have concentrations in intervals (e.g., 10% intervals) ranging from 0% to 100% methanol. Because the method 100 relies on the surface tension of the various concentrations of a liquid (e.g., a methanol solution), surface tension of the aqueous methanol solutions of the various concentrations needs to be determined. To illustrate, accurate density data may be first measured to precisely measure the surface tension of the aqueous methanol solutions. Densities of various concentrations of the aqueous methanol solutions may be measured using calibrated stainless steel Pycnometers. In some example embodiments, the measured densities of the various concentrations of the aqueous methanol solutions may be compared against literature data to verify the reliability of the measured density values.

After the densities of the various concentrations of the aqueous methanol solutions are measured, the corresponding surface tensions of the known density aqueous methanol solutions may be measured, for example, using a pendant drop method or other methods known to those of ordinary skill in the art. Again, the measured surface tension values may be compared against literature data to verify the reliability of the measured surface tension values. The density and surface tension measurements may be performed at a temperature (e.g., room temperature, i.e., 70° F.) and atmospheric conditions that match the temperature and atmospheric conditions during the implementation of other steps of the method 100.

At step 102, the method 100 includes placing solid particles in a container made of a very high surface energy material. For example, about 0.05 gm of solid particles (e.g., glass beads) may be placed in a Petri dish. As indicated above, the method 100 is illustratively described herein using glass beads as the solid particles of which the surface energy is measured. To illustrate, batches of glass beads having sizes that fall in different size ranges are used as the solid particles. Within each size range of the glass beads, some of the glass beads are treated to be hydrophobic, other glass beads are treated to be intermediate-wet, and yet others are untreated leaving them hydrophilic. In general, a hydrophilic solid particle tends to sink in water faster than an equivalent hydrophobic solid particle. To illustrate the step 102 of the method 100 with respect to glass beads, glass beads having sizes that fall within a particular range of sizes may be placed in the container at step 102. For example, the container may be an ordinary Petri dish or a wedge floatation device illustrated in FIG. 6. To illustrate, the Petri dish may be made from glass, which is a very high surface energy material.

To obtain batches of the glass beads based on glass bead sizes, solid particle size measurements of glass beads may be performed by following an American Society for Testing and Materials (ASTM) standard method, such as Tyler sieving method.

To illustrate, a sample of 16-20 mesh (850-1180 µm) size glass beads may be obtained by sieving feed glass beads that are in the size fraction of 12-20 mesh (850-1400 µm). For example, sieving of the feed glass beads can be performed using a standard sieve shaker (e.g., RO-TAP, RX-29, 60 Hz), for example, for 15 minutes for each batch of glass beads. A volume of feed glass beads can be chosen according to the mesh size range of the particular battery of sieves. Further, 50-70 mesh (212-300 µm) size fraction glass beads can be sieved to obtain 60-70 mesh (212-250 µm) size fraction of the glass beads. Further, 170-325 mesh (45-90 µm) size glass bead samples can be obtained by using standard splitting procedure on a larger sample of glass beads using methods known to those of ordinary skill in the art. In some example embodiments, sieve cleaning for 50-70 mesh (212-300 µm) size can be performed using, for example, an ultrasonicator for approximately 30 minutes per sieve. The sieves may then be dried in an oven, for example, for 60 minutes at approximately 105° C. For coarse mesh sieves (i.e., 16-20 mesh (850-1400 µm) size), the plugged particles may be removed according to the ASTM standard procedure using a paint brush with 1 inch long bristles.

Density measurement of glass beads may be conducted by displacement and Pycnometry methods. As an illustrative example of the displacement method, about 2 cubic centimeter (cc) of water may be taken in a 5 cc graduated cylinder with 0.1 cc resolution, and the exact volume and weight (cylinder+water) of the water may be measured. Small amount of glass beads may be added to the water in the cylinder, such that the water volume rises to about 4 cc, and the increase in the water volume and the weight (glass beads+cylinder+water) are measured. The increase in the water volume is the volume of the glass beads added and the difference in the weights is the weight of the glass beads. The density may be calculated using the conventional mass over volume formula as known to those of ordinary skill in the art. In some example embodiments, each measurement may be repeated for a minimum of three times and the average value may be calculated. As an alternative or in addition to the displacement method described above, Pycnometer method using methanol as a liquid that completely wets the glass beads can also be used to measure the densities of the glass beads.

In the Pycnometer method, empty weight of a well calibrated stainless steel Pycnometer are first measured in grams and are represented by W1 in Equation 1 below. Then, the weight of Pycnometer plus glass beads (W2), weight of Pycnometer plus glass beads plus liquid (W3), and weight of Pycnometer plus liquid (W4) may be measured in grams in order to calculate the density of beads using Equation 1.

$$\rho_{beads} = \rho_{liquid}\left(\frac{(W2-W1)}{(W4-W1)-(W3-W2)}\right) \quad \text{Equation 1}$$

where, $\rho_{liquid}$ (in g/cc) is the density of liquid used.

In an example embodiment, the average density of the glass beads is determined to be approximately 2.49 g/cc based on the displacement and the Pycnometery methods described above, which is equal to the density of soda-lime glass reported in some literatures.

In some example embodiments, the sieved glass beads may be washed to remove impurities on the surface of the glass beads that may result from the use of stainless steel sieves. For example, the sieved glass beads may be washed with 3 molar hot (60° C.) hydrochloric acid for approximately 30 minutes and then rinsed with deionized water until the pH of the effluent water becomes neutral (i.e., equal to that of the deionized water). In some example embodiments, the cleaned glass beads may be dried in an oven at 60° C. for about 12 hours.

In some example embodiments, the three different sized cleaned glass beads (i.e., 45-90 µm, 212-250 µm, and 850-1180 µm) and three soda-lime glass discs (e.g., 1 inch diameter and 0.126 inch thickness soda-lime glass discs) may undergo wettability alteration treatment to make the three different sized cleaned glass beads and the corresponding soda-lime glass discs hydrophobic. For example, some of the glass beads in each of the size ranges (i.e., 45-90 µm, 212-250 µm, and 850-1180 µm) may be surface treated using organosilane to obtain hydrophobic glass beads. Wettability alteration of the soda-lime glass discs can be performed to facilitate the direct contact angle measurement using sessile drop method. Some of the cleaned glass beads of each of the size ranges remain untreated (i.e., without wettability alteration) and are thus hydrophilic.

Intermediate-wet glass beads and soda-lime glass discs may be prepared using chlorotrimethylsilane and toluene. For example, 40 ml of chlorotrimethylsilane (>99%) and 100 ml of toluene may be added to a round bottom flask containing 20 grams of glass beads. Reflux chemical reaction may be performed, for example, for 24 hours, followed by the silanized glass beads and soda-lime glass discs may be rinsed with methanol and dried by heating in an oven at 110° C. Thus, using the illustrative example steps described above, glass beads falling under three size ranges (i.e., 45-90 µm, 212-250 µm, and 850-1180 µm), with each size range having at least hydrophobic, intermediate-wet, and hydrophilic batches of beads, may be prepared.

Continuing with step 104 of the method 100, the method 100 includes pouring a liquid into the container at step 104 after placing solid particles in the container made of the very high surface energy material at step 102. Alternatively, the solid particles may be placed in the container made of the very high surface energy material after first pouring the liquid in the container. As an illustrative example, about 0.05 gram of solid particles (e.g., about 0.05 gram glass beads prepared as described above) may be placed on the surface of a known surface tension liquid that is placed (e.g., poured) in a Petri dish of, for example, about 100 mm diameter and 20 mm height.

The step 104 of the method 100 may be repeated for different size ranges and wettability of solid particles (e.g., glass beads prepared as described above) using a liquid with different percentage of water. To illustrate, different concentrations of aqueous methanol solutions may be used as the liquid in step 104 during different iterations of the method 100. As described above, because the method 100 relies on the surface tension of the various concentrations of the liquid used in step 104, the surface tension of the liquid needs to be known or determined. For example, surface tension of a particular concentration of aqueous methanol solutions may be determined based on the density of the particular concentration of aqueous methanol solution measured as described above. For example, for different iterations of the method 100, different concentrations of the aqueous methanol solution may be used. As an illustrative example, the liquid used in step 104 during a first iteration of the method 100 to determine the surface energy of solid particles may include 0% methanol (i.e., 100% water), and an immediately subsequent iteration of the method 100 may use a liquid that has 10% concentration of the methanol (i.e., 90% water). In some example embodiments, the concentration of methanol in the liquid, (i.e., in the aqueous methanol solution) may be increased in subsequent iterations of the method 100, for example, until the liquid used in step 104 is 100% methanol. For example, concentrations of methanol in the liquid may be increased in intervals of, for example, 10% during each subsequent iteration. In some alternative embodiments, the liquid used in a first iteration of the method 100 to determine the surface energy of solid particles may have 100% methanol, and the concentration of methanol may be lower (for example, by 10%) in each subsequent iteration until the concentration of methanol in the liquid used in step 104 is 0%. In some example embodiments, the concentration of methanol used in step 104 may not be varied to 0% and/or 100%, and other ranges of the concentration of methanol (or another liquid) may be used.

At step 106, the method 100 includes tilting the container to drain out from the container a first subset of the solid particles floating at a top surface of the liquid. For example, after the liquid (e.g., the aqueous methanol solution) is poured into the container at step 104, some of the solid particles (e.g., glass beads belonging to a particular size range and having a particular wettability) may float in the liquid. Thus, at step 106, the container is tilted to drain out some of the liquid out of the container such that at least some of the floating particles (e.g., glass beads) are also drained out.

At step 108, the method 100 includes tilting the container to move the liquid away from a second subset of the solid particles that are below the top surface. To illustrate, after a portion of the liquid is drained out along with at least some of the floating particles, the container (e.g., Petri dish) is tilted to an angle such that the remaining liquid is still in the Petri dish, but some or all of the solid particles that sank in the liquid come out of the formed liquid wedge.

At step 110, the method 100 includes tilting the container to move the liquid back toward the second subset of the solid particles such that at least a portion of the second subset of particles floats at the top surface of the liquid. To illustrate, after the container is tiled to move the liquid away from the second subset of the solid particles that are below the top surface (e.g., solid particles not floating at the top surface of the liquid or that are sunk), the container may be turned slowly to a horizontal position such that the wedge of the liquid approaches and touches the solid particles (e.g., glass beads) at their contact surfaces with the container (e.g., the Petri dish) so that the glass beads may be slowly lifted on top of the liquid.

At step 112, the method 100 includes tilting the container to drain out from the container the portion of the second subset of the solid particles now floating at the top surface of the liquid. To illustrate, step 110 may result in at least some of the second subset of the solid particles (e.g., solid particles that were previously sunk) to float at the surface of the liquid. Thus, the container may be tilted at step 112 to drain out some of the liquid such that some of the now floating solid particles are drained out of the container.

In some example embodiments, the method 100 may include repeating steps 108, 110, and 112 until substantially all floatable particles of the solid particles are floated by the liquid. That is, tilting the container to move the liquid away from the second subset of the solid particles at step 108, tilting the container to move the liquid back toward the second subset of solid particles at step 110, and tilting the container to drain out from the container the portion of the second subset of the solid particles now floating at the top surface of the liquid at step 112 may be repeated until substantially all floatable solid particles of the solid particles are drained out of the container. If the amount of liquid in the container becomes insufficient to perform steps 108, 110, and 112 until all floatable solid particles are floated by the liquid, the method 100 includes adding more liquid of the same concentration to the container to repeat steps 108, 110, and 112 until all floatable solid particles are floated by the liquid.

After substantially all floatable solid particles are drained out of the container, the method 100 may include repeating steps 102-112 with a different concentration of the liquid (e.g., increasing concentration of methanol in the aqueous methanol solution used as the liquid). To illustrate with respect to aqueous methanol solution being used as the liquid, in each iteration of the method 100, an amount of the solid particles from the same batch of solid particles used in a prior iteration is used to identify the transition surface tension of the liquid where floating particles become sinking particles due to the reduction of the surface tension of the liquid as the concentration of methanol is increased for each iteration. As described above, because surface tension for different concentrations of the liquid (e.g., for different percentages of methanol in aqueous methanol solution) are known or determined as described above, the different concentrations of the liquid right before and right after the floating particles become sinking particles due to the reduction of the surface tension of the liquid are used to determine the transition surface tension of the liquid.

As described above, when using aqueous methanol solutions in the implementation of the method 100, surface tension of the aqueous methanol solution is changed from one iteration to another iteration of the method 100 by using different concentrations of the aqueous methanol solution, such as by increasing from 0% methanol (i.e., 100% water) to 100% methanol (i.e., 100% methanol. Although aqueous methanol solution is given as an example of the liquid used in the method 100, in alternative embodiments, other solutions may be used. Further, the change in the concentration of, for example, methanol may be changed in fixed or varying amounts from one iteration to another. Further, in some alternative embodiments, the concentration of methanol or another liquid in the liquid/solution used at step 102 of the method 100 may be decreased for each iteration of steps 102-112 where the method 100 is used to determine the transition surface tension of the liquid based on substantially all sinking particles in one iteration floating in an immediately subsequent iteration.

For ideal solid particles, i.e., where all of the solid particles have the same shape, size, wettability, surface roughness, etc., a curve representing percentage of floating particles (e.g., on y-axis) vs. surface tension of the liquid used at step 102 of the method 100 (e.g., on x-axis) would have a sudden transition (vertical straight line) from "all floating" particles to "all sinking" particles. Surface energy of the particles should be almost equal to the surface tension of the liquid used in step 102 and on which the solid particles just sink.

Figure 2:
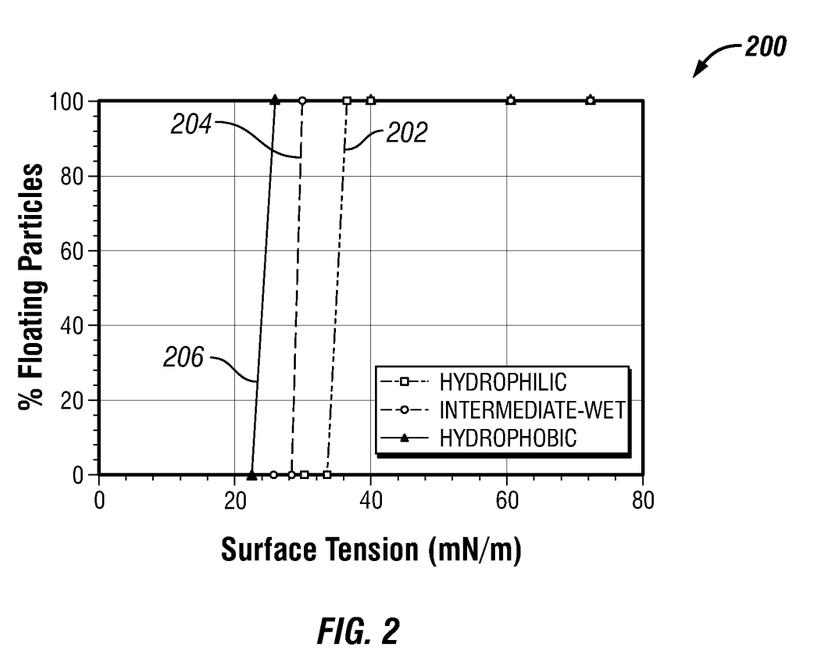
FIG. 2 illustrates a surface energy measurement graph for hydrophilic, intermediate-wet and hydrophobic glass of 850-1180 µm size range according to an example embodiment.

FIG. 2 illustrates a surface energy measurement graph 200 for hydrophilic, intermediate-wet, and hydrophobic glass of 850-1180 μm size range according to an example embodiment. For example, the graph 200 may be generated based of the method 100. As illustrated in FIG. 2, for solid particle (i.e., glass bead) sizes in the range of 850-1180 μm, the respective transition lines 202, 204, 206 from 100% floating to 0% floating are almost nearly vertical and different for hydrophilic, intermediate-wet, and hydrophobic solid particles, suggesting that the size range does not significantly influence the floating behavior of the glass beads compared to the wettability (or surface energy) of the glass beads. Further, the floating behaviors of the hydrophilic, intermediate-wet, and hydrophobic particles are clearly distinguished.

As illustrated in FIG. 2, 100% of the hydrophilic glass beads of the 850-1180 μm size range placed on 50% (v/v) aqueous methanol solution (corresponding to surface tension of 36.6 mN/m) are floating and 100% of the glass beads are sinking into the 60% (v/v) aqueous methanol solution (corresponding to surface tension of 33.5 mN/m). The range between surface tension of 36.6 mN/m and surface tension of 33.5 mN/m may be narrowed down using the method 100 that iteratively uses aqueous methanol solutions having methanol concentrations ranging between 50% and 60% in water. For example, if the method 100 is implemented by increasing the concentration of methanol by 1 percentage point (e.g., from 50% to 51% methanol until 60% methanol), a more accurate surface energy of the solid particles that is very closely approximated by the transition surface tension of the aqueous methanol solutions where "all floating" glass beads become "all sinking" glass beads.

As shown in FIG. 2, 100% of the intermediate-wet particles are floating on 70% aqueous methanol solution (corresponding to surface tension of 29.8 mN/m) and 0% of the particles are floating on 80% aqueous methanol solution (corresponding to surface tension of 28.3 mN/m). In the case of hydrophobic particles, 100% particles are floating on 90% aqueous methanol solution (corresponding to surface tension of 25.9 mN/m) and 100% sinking on 100% methanol (corresponding to surface tension of 22.6 mN/m). As stated above, the surface tension of the liquid (e.g., the surface tension of the aqueous methanol solution) may transition wherein "all floating" solid particles become "all sinking" solid particles during the iterative implementation of steps 102-112 of the method 100 is considered a close approximate of the surface energy of the solid particles and a quantification of the wettability of the solid particles.

Figure 3:
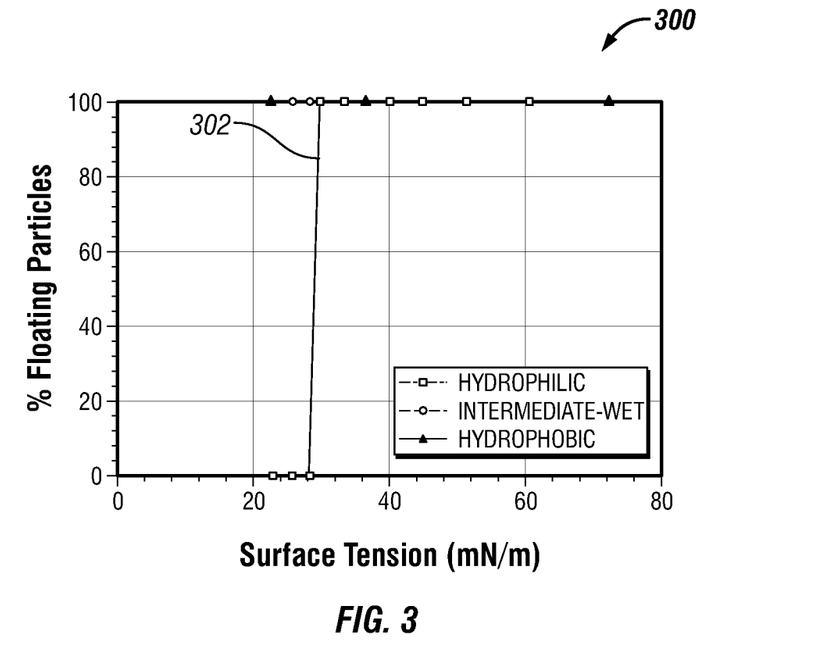
FIG. 3 illustrates a surface energy measurement graph for hydrophilic, intermediate-wet and hydrophobic glass beads of 212-250 µm size range according to an example embodiment.

FIG. 3 illustrates a surface energy measurement graph 300 for hydrophilic, intermediate-wet and hydrophobic glass beads of 212-250 μm size range according to an example embodiment. For example, the graph 300 may be generated based of the method 100. As illustrated in FIG. 3, 100% of both the intermediate-wet and hydrophobic particles are floating on 100% methanol, suggesting that the surface energies of these particles are lower than the surface tension of the 100% methanol solution. However, 100% of the hydrophilic particles are sinking in 80% aqueous methanol solution and 100% of the particles are floating on 70% aqueous methanol solution as illustrated by a transition line 302.

Figure 4:
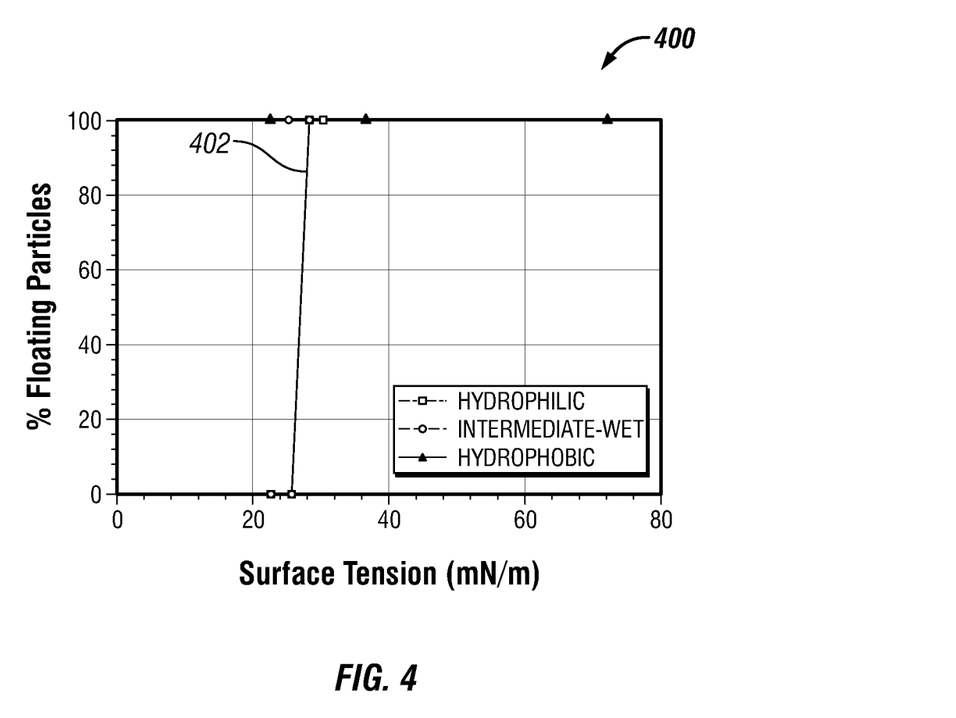
FIG. 4 illustrates a surface energy measurement graph for hydrophilic, intermediate-wet and hydrophobic glass of 45-90 µm size range according to an example embodiment.

FIG. 4 illustrates a surface energy measurement graph 400 for hydrophilic, intermediate-wet, and hydrophobic glass of 45-90 μm size range according to an example embodiment. For example, the graph 400 may be generated based of the method 100. As illustrated in FIG. 4, 100% of both the intermediate-wet and hydrophobic particles of the size range 45-90 µm are floating on 100% methanol similar to the 212-250 µm size range solid particles. However, the transition line 402 indicating the transition in surface energy corresponding to 100% floating to 100% sinking of the hydrophilic solid particles is between 80% and 90% aqueous methanol solutions.

Figure 5A:
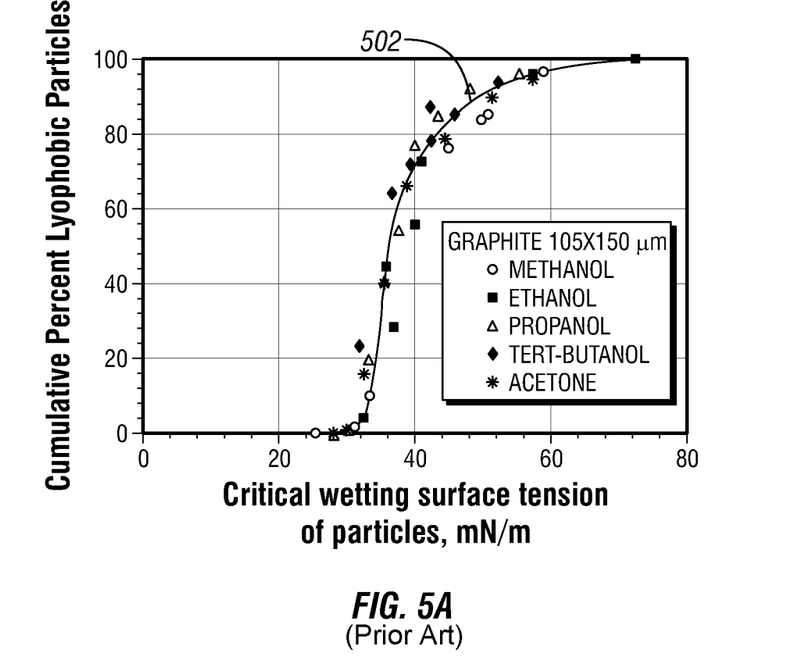
FIGS. 5A and 5B illustrate surface energy measurement graphs corresponding to the conventional method and the method of FIG. 1, respectively, according to an example embodiment.
Figure 5B:
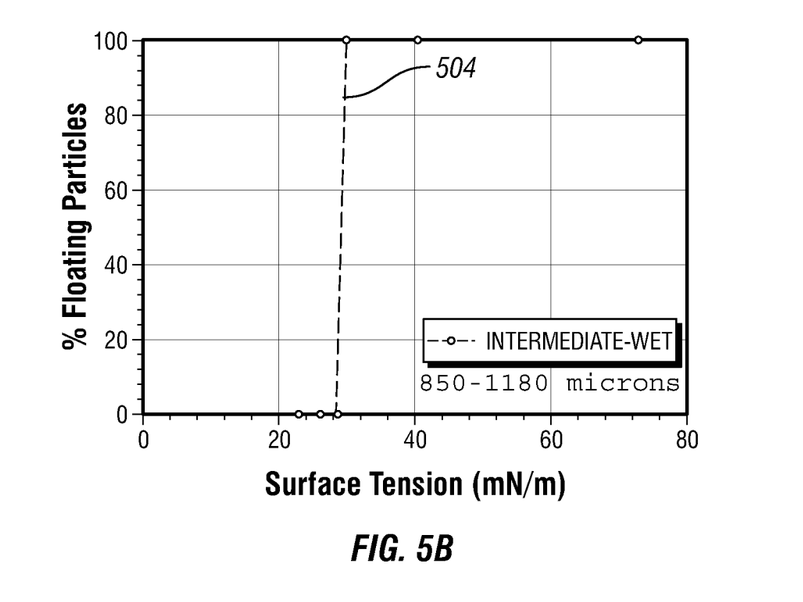

FIGS. 5A and 5B illustrate graphs showing surface energy measurement graphs corresponding to a conventional method and the method 100 of FIG. 1, respectively, according to an example embodiment. As shown in FIG. 5A, the curve 502 has a substantially S-shape illustrating large uncertainty in the measured surface energy of the graphite particles. To illustrate, the surface energy of the graphite particles, which have sizes in the range of 106-150 µm, ranges from approximately 72 mN/m to 30 mN/m. In contrast, the curve 504 in FIG. 5B, corresponding to the surface energy of intermediate-wet glass beads having sizes in the range of 850-1180 µm, has a nearly vertical straight line transition portion. Thus, the method 100 provides results that have less uncertainty than results determined using conventional methods such as the Film Floatation Technique.

Figure 6:
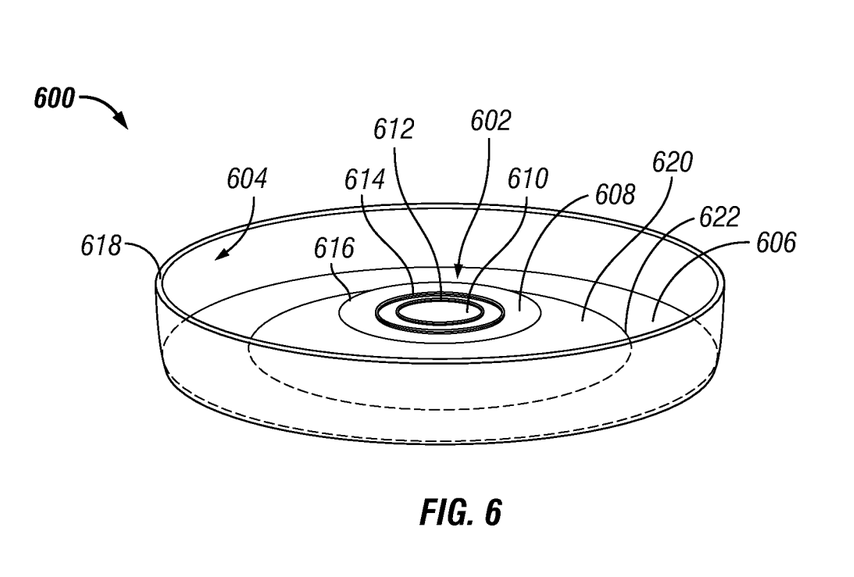
FIG. 6 is a wedge floatation device for use in determining solid particle surface energy according to an example embodiment.

FIG. 6 is a wedge floatation device 600 for use in determining solid particle surface energy according to an example embodiment. The wedge floatation device 600 includes a bottom section 602 and a sidewall 604. The sidewall 602 is positioned around a perimeter of the bottom section 602 to contain a liquid within the wedge floatation device 600. In some example embodiments, the bottom section 602 may include an outer portion 606 and a plateau portion 608. For example, the plateau portion 608 may be centrally positioned in the bottom section 602. The plateau portion 608 may be raised to a height above the outer portion 606 and below a top edge 618 of the sidewall 604. For example, a height of the plateau section 608 may be approximately 50% to 75% of a height of the device 600. In alternative embodiments, the height of the plateau section 608 may be outside the range of 50% to 75% of the height of the device 600.

In some example embodiments, the plateau portion 608 includes an inner groove 612 and an outer groove 614. Alternatively, the plateau portion 608 may include just one groove or more than two grooves. In some example embodiments, the inner groove 612 and the outer groove 614 may be substantially concentric with an outer perimeter 616 of the plateau portion 608. Each of the inner groove 612 and the outer groove 614 is designed to dampen the velocity of a liquid directed from the outer perimeter 616 of the plateau portion 608 to a center of the plateau portion 608. As illustrated in FIG. 6, the inner groove 612 surrounds a central portion 610 of the plateau portion 608. In some example embodiments, the central portion 610 of the plateau portion 608 has a substantially flat surface. Further the inner groove 612 and the outer groove 614 are spaced from each other such that a liquid that reaches inner groove 612 after passing the outer groove 614 travels on a section of the plateau portion 608 between the inner groove 612 and the outer groove 614. For example, the section of the plateau between the inner groove 612 and the outer groove 614 may have a substantially flat surface.

In some example embodiments, the bottom section 602 may include a transition portion 620 extending between the outer portion 606 and the plateau portion 608. For example, the transition portion 620 may surround the outer perimeter 616 of the plateau portion 608, and the outer portion 606 may surround a perimeter 622 of the transition portion 620. In some example embodiments, the transition portion 620 may be slanted at an angle relative to a vertical axis that is perpendicular to the outer portion. For example, the angle may range between 10 degrees and 85 degrees. In some alternative embodiments, the transition portion 620 may be perpendicular to the outer portion 606 and to the plateau portion 608. For example, the transition portion 620 may extend in a substantially vertical direction between the outer portion 606 and to the plateau portion 608.

In some example embodiments, the sidewall 604 may be perpendicular to the outer portion 606 of the bottom section 602. Alternatively, the sidewall 604 may be at an obtuse angle or at an acute angle relative to the outer portion 606 of the bottom section 602.

In some example embodiments, the wedge floatation device 600 is made from glass in a manner known to those of ordinary skill in the art. Alternatively, the wedge floatation device 600 is made from other materials that have very high surface energy. Further, the wedge floatation device 600 may be scaled down or scaled up as needed based on the application. For example, the wedge floatation device 600 may have a diameter similar to an ordinary laboratory Petri dish. Alternatively, the wedge floatation device 600 may be sized for industrial applications, for example, related to the oil and gas industry.

In some example embodiments, the wedge floatation device 600 may be used to implement the method 100 of FIG. 1. To illustrate, solid particles for which the surface energy is to be measured, may be placed in the central portion 610 of the plateau portion 608 that is surrounded by the inner groove 612. A liquid with a known (e.g., previously determined) surface tension may be slowly added in annular space of the wedge floatation device 600 between the plateau portion 608 and the sidewall 604. Once the liquid level reaches to the top edge of the plateau portion 608, the liquid starts approaching the outer groove 614 followed by the inner groove 612. Both the outer and inner grooves 612, 614 help in dampening the approaching circular wedge velocity and help in making the approaching liquid wedge uniform so that the liquid wedge approaches the beads substantially equally (like a diminishing circle) from all sides. The floatable particles of the solid particles placed in the central portion 610 of the plateau portion 608 are slowly supported and lifted by the circular wedge of the liquid. After floatable particles are lifted up, other steps of the method 100, such as the method 106-112 may be implemented using the wedge floatation device 600.

Although some embodiments have been described herein in detail, the descriptions are by way of example. The features of the embodiments described herein are representative and, in alternative embodiments, certain features, elements, and/or steps may be added or omitted. Additionally, modifications to aspects of the embodiments described herein may be made by those skilled in the art without departing from the spirit and scope of the following claims, the scope of which are to be accorded the broadest interpretation so as to encompass modifications and equivalent structures.

What is claimed is:

1. A wedge floatation device, comprising:
   a bottom section; and
   a sidewall positioned around a perimeter of the bottom section to contain a liquid within the wedge floatation device, wherein the bottom section comprises:
   an outer portion;
   a plateau portion centrally positioned in the bottom section, wherein the plateau portion is raised to a height above the outer portion and below a top edge of the sidewall, wherein the plateau portion includes a groove that is substantially concentric with an outer perimeter of the plateau portion, and wherein the groove is designed to dampen the velocity of a liquid directed from the outer perimeter of the plateau portion to a center of the plateau portion; and a transition portion extending between the outer portion and the plateau portion, wherein the transition portion surrounds the outer perimeter of the plateau portion, wherein the outer portion surrounds a perimeter of the transition portion, wherein the outer perimeter of the plateau portion extends horizontally inward at the height below the top edge of the sidewall, and wherein the transition portion is slanted at an angle relative to a vertical axis that is perpendicular to the outer portion, the angle ranging between 10 degrees and 85 degrees.

2. The device of claim 1, wherein a section of the plateau portion that is surrounded by the groove has a substantially flat surface.

3. The device of claim 1, wherein the plateau portion further includes one or more additional grooves positioned between the outer perimeter of the plateau portion and the groove and wherein the one or more additional grooves are substantially concentric with the groove.

4. The device of claim 1, wherein the sidewall is perpendicular to the outer portion.

5. The device of claim 1, wherein the sidewall is at an obtuse angle relative to the outer portion.

6. The device of claim 1, wherein the sidewall is at an acute angle relative to the outer portion.

7. The device of claim 1, wherein the groove is separated from the outer perimeter of the plateau portion by a flat section of the plateau portion, the flat section being at the height below the top edge of the sidewall.

8. The device of claim 1, wherein the outer portion includes a flat section extending between the sidewall and the transition portion.

9. A wedge floatation device, comprising:
a bottom section; and
a sidewall positioned around a perimeter of the bottom section to contain a liquid within the wedge floatation device, wherein the bottom section comprises:
an outer portion;

a plateau portion centrally positioned in the bottom section, wherein the plateau portion is raised to a height above the outer portion and below a top edge of the sidewall, wherein the plateau portion includes a groove that is substantially concentric with an outer perimeter of the plateau portion, and wherein the groove is designed to dampen the velocity of a liquid directed from the outer perimeter of the plateau portion to a center of the plateau portion; and a transition portion extending between the outer portion and the plateau portion, wherein the transition portion surrounds the outer perimeter of the plateau portion, wherein the outer portion surrounds a perimeter of the transition portion, wherein the outer perimeter of the plateau portion extends horizontally inward at the height below the top edge of the sidewall, and wherein the height of the plateau portion is approximately 50% to 75% of a height of the wedge floatation device.

10. A wedge floatation device, comprising:
a bottom section; and
a sidewall positioned around a perimeter of the bottom section to contain a liquid within the wedge floatation device, wherein the bottom section comprises:
an outer portion;
a plateau portion centrally positioned in the bottom section, wherein the plateau portion is raised to a height above the outer portion and below a top edge of the sidewall, wherein the plateau portion includes a groove that is substantially concentric with an outer perimeter of the plateau portion, and wherein the groove is designed to dampen the velocity of a liquid directed from the outer perimeter of the plateau portion to a center of the plateau portion; and a transition portion extending between the outer portion and the plateau portion, wherein the transition portion surrounds the outer perimeter of the plateau portion, wherein the outer portion surrounds a perimeter of the transition portion, wherein the outer perimeter of the plateau portion extends horizontally inward at the height below the top edge of the sidewall, and wherein the wedge floatation device is made from glass.

* * * * *